(12) United States Patent
Arata

(10) Patent No.: US 7,359,746 B2
(45) Date of Patent: Apr. 15, 2008

(54) IMAGE GUIDED INTERVENTIONAL METHOD AND APPARATUS

(75) Inventor: Louis K. Arata, Mentor, OH (US)

(73) Assignees: Z-Kat, Inc., Ft. Lauderdale, FL (US); Biomet Inc., Warsaw, IN (US)

( * ) Notice: Subject to any disclaimer, the term of this patent is extended or adjusted under 35 U.S.C. 154(b) by 790 days.

(21) Appl. No.: 10/658,110

(22) Filed: Sep. 9, 2003

(65) Prior Publication Data

US 2004/0127788 A1 Jul. 1, 2004

Related U.S. Application Data

(60) Provisional application No. 60/409,339, filed on Sep. 9, 2002.

(51) Int. Cl.
*A61B 5/05* (2006.01)

(52) U.S. Cl. ............ 600/424; 606/130; 600/426; 600/427

(58) Field of Classification Search ........ 600/424, 600/426, 427, 429; 606/130
See application file for complete search history.

(56) References Cited

U.S. PATENT DOCUMENTS

| | | | |
|---|---|---|---|
| 5,587,937 A | 12/1996 | Massie et al. | |
| 5,625,576 A | 4/1997 | Massie et al. | |
| 5,898,599 A | 4/1999 | Massie et al. | |
| 6,377,011 B1 | 4/2002 | Ben-Ur | |
| 6,405,158 B1 | 6/2002 | Massie et al. | |
| 6,490,473 B1 * | 12/2002 | Katznelson et al. | 600/410 |
| 6,494,039 B2 | 12/2002 | Pratt et al. | |
| 6,546,279 B1 * | 4/2003 | Bova et al. | 600/429 |
| 6,704,694 B1 | 3/2004 | Basdogan et al. | |
| 6,782,287 B2 * | 8/2004 | Grzeszczuk et al. | 600/424 |
| 6,786,896 B1 | 9/2004 | Madhani et al. | |
| 6,837,892 B2 * | 1/2005 | Shoham | 606/130 |
| 6,853,965 B2 | 2/2005 | Massie et al. | |
| 2002/0077543 A1 * | 6/2002 | Grzeszczuk et al. | 600/424 |

OTHER PUBLICATIONS

Search Report (PCT/US03/28161) Jun. 4, 2004, 7 pgs.

* cited by examiner

*Primary Examiner*—Brian L. Casler
*Assistant Examiner*—Joel Lamprecht
(74) *Attorney, Agent, or Firm*—Fay Sharpe LLP

(57) ABSTRACT

In accordance with an embodiment of the present invention, an image guided interventional system enables registration of a patient, preferably automatically and without an explicit patient registration step, to newly acquired images as the patient is moved out of the imager. Only one set of images has to be taken. The position of the needle or other instrument is tracked using a tracking system and its position continually displayed and updated with respect to the images. Therefore, there is no need to take additional images for purposes of tracking progress of an instrument being inserted into a patient. Avoiding additional scans saves time and reduces exposure of the patient to radiation.

16 Claims, 3 Drawing Sheets

IMAGE GUIDED INTERVENTIONAL METHOD AND APPARATUS

RELATED APPLICATION

This patent application claims the benefit of U.S. Provisional Application Ser. No. 60/409,339, filed on Sep. 9, 2002, entitled "Image Guided Interventional Method and Apparatus," the disclosure of which is incorporated herein by reference.

FIELD OF THE INVENTION

The invention pertains generally to image-guided apparatus and methods for performing interventional procedures.

BACKGROUND OF THE INVENTION

Tissue biopsies, one type of interventional procedure, are usually performed on an out-patient basis by sedating a patient and inserting a needle through the skin and into the tissue of interest. To increase success, a medical imaging device, which will be generally referenced as an "imager," is used to guide needles to a target area in the patient, from which a tissue biopsy is to be taken. Any one or more of various different types of imaging modalities may be used depending on a number of factors, including tissue type, anatomic characteristics of the target tissue, biopsy technique for optimal sampling of the target tissue, physician preference, the modality that allows for safe and accurate placement of biopsy needle with documentation that the biopsy specimen was obtained from the target tissue, and lesion conspicuity and visualization of adjacent anatomic structures.

In a typical image guided biopsy procedure, a patient is placed on a couch of an imager in the position that yields the greatest access to the pathology and is mildly sedated. The couch moves the patient into and out of the field of view of the imager. The patient is scanned in this position to locate the approximate region of the area of interest, such as a suspected tumor. Once these images are reviewed, an externally applied marker is affixed to the patient to identify the location of interest, and additional images of just this area are taken.

Interventional procedures such as tissue biopsies are preferably performed outside of the imager. Typically, the size and/or shape of the image does not allow for the procedure to be performed inside the imager. Therefore, after obtaining these localization images, the patient is removed from the imager and the site for insertion of a biopsy needle is prepped and draped for incision. The patient is administered a local anesthetic at the site of the needle entry and a radiologist begins to place the needle into position. To confirm proper trajectory of the needle, the patient is moved back into the imager and images are acquired at the site of entry of the needle. The needle appears in the images. Once this status image is taken, the patient is removed from the imager and the needle is advanced along the trajectory. As the needle continues to be inserted, the patient is repeatedly moved or backed into the imager to capture additional images to confirm the trajectory and position of the needle, until the radiologist confirms that the tip of the biopsy needle is at the target tissue. Sample extraction then occurs and the tissue is sent to pathology for analysis of cells.

This conventional image guided procedure is very time consuming and involves a great deal of time to acquire the images and radiation exposure to the patient. In addition, the methodology is not well defined and requires a fairly steep learning curve.

Several types of systems have been developed to improve the targeting for a biopsy procedure. For example, one system uses a mechanical arm to hold the needle. The position of the arm is registered with the coordinate space of the imager, meaning that the position of the arm, and thus a needle held by it, is known with reference to a diagnostic image of the patient that is taken while the patient is on a couch that moves in and out of the imager. In another example, an MR imager incorporates a system in which the position of a biopsy needle is continuously tracked and displayed on images. However, in order to maintain registration between the patient and the images, the procedure must be performed inside the scanner. Furthermore, the needle tracking component can only be used with the particular MR imaging system.

BRIEF SUMMARY OF THE INVENTION

The invention provides improved image guided interventional systems and methods, which overcome one or more of the problems with prior systems. Various aspects of a preferred embodiment of the invention are described below in connection with an example of an image guided interventional system and imager.

Briefly, one aspect of the exemplary image guided interventional system enables registration of a patient, preferably automatically and without an explicit patient registration step, to newly acquired images as the patient is moved out of the imager. Only one set of images has to be taken. The position of the needle or other instrument is tracked using a tracking system and its position continually displayed and updated with respect to the images. Therefore, there is no need to take additional images for purposes of tracking progress of an instrument being inserted into a patient. Avoiding additional scans saves time and reduces exposure of the patient to radiation.

Another aspect of the exemplary image guided interventional system uses a calibration procedure for determining the spatial relationship between images taken by the image and a reference point on the imager, thus allowing the system to be used with an imager and images taken by the imager. The calibration process enables the system to work with any type of 2D or 3D imager, including without limitation those that use computed tomography (CT), magnetic resonance (MR), SPECT, positron emission tomography (PET) and fluoroscopy, or combinations thereof. The image guided interventional system need not, therefore, be limited to a particular imager.

DETAILED DESCRIPTION OF THE DRAWINGS

The various aspects of the invention, in their preferred embodiment, are described below with reference to image guided interventional system working with a three-dimensional medical imaging system, which will be referenced to as a scanner. Though particularly useful with a three-dimensional imager or any imaging system in which a patient is moved, the image guided interventional system can be adapted for use with a two-dimensional imager.

Figure 1:
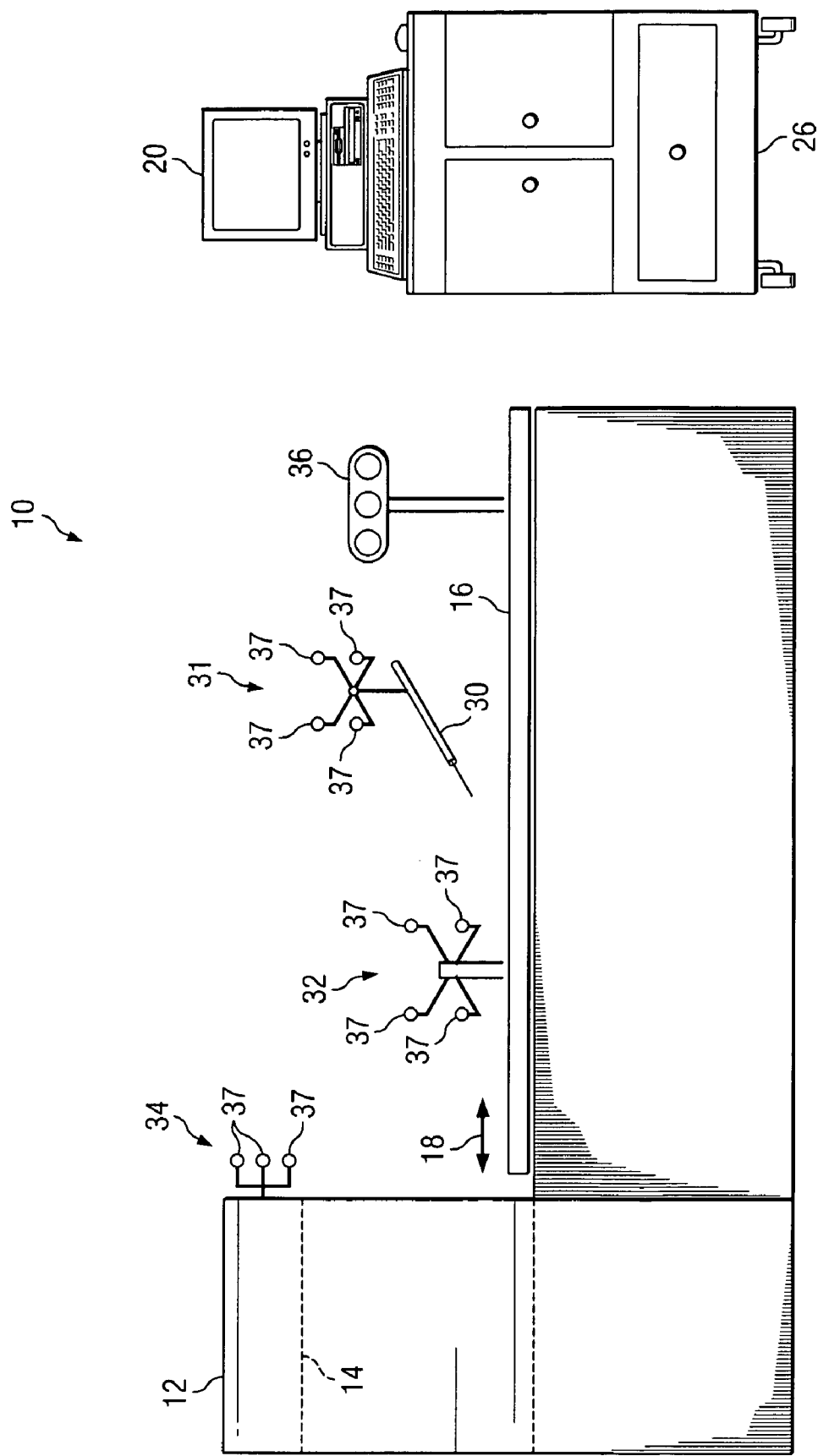
FIG. 1 is a schematic representation of a three dimensional medical imaging system with an image guided interventional system.

As shown in FIG. 1, a typical three-dimensional medical imaging system 10, such as a MR or CT scanner, has a doughnut-shaped portion that contains a scanner 12 having a central bore 14 (indicated by dashed lines) through which a patient being scanned passes. The structure of scanner 12 is also referred to as a gantry. The patient lies on a movable platform 16, which is referred to as a table or "couch". The platform transports the patient into bore 14 and back out of it along a straight path, generally indicated by arrow 18. A scan typically generates a set of two-dimensional, parallel images called "slices" taken at equally-spaced intervals through an area of interest of the patient, along a line parallel to the movement of the couch. Collectively, these slices constitute a three-dimensional image volume of the patient's anatomy, with each picture element in each slice having a three-dimensional coordinate. For interventional procedures, one or more monitors or other display devices 20 are positioned near the couch for receiving and displaying image slices from the scanner.

Figure 2:
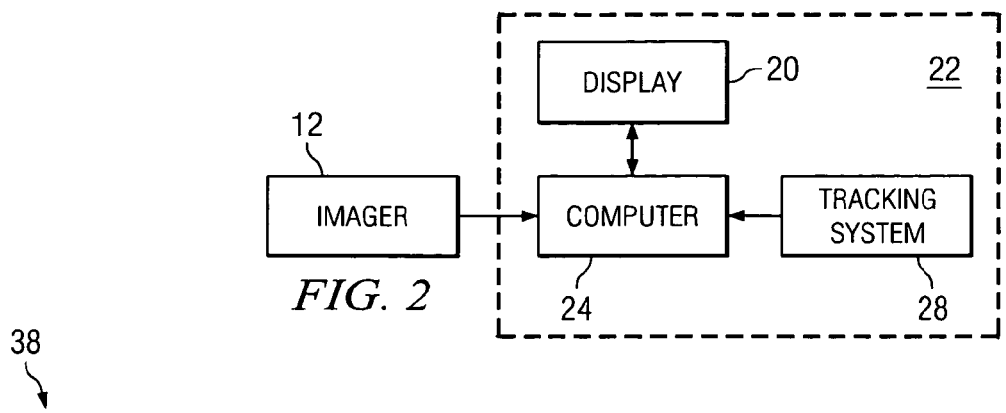
FIG. 2 is a schematic drawing of image guided interventional system and an imager illustrating flow of information.

Referring now to FIGS. 1 and 2, it is preferred that display device 20 is part of an image guided interventional system 22. This system is typically comprised of at least one computer 24 running one or more computer programs. Computer 24 is preferably, but not necessarily, located on a cart or cabinet 26. In order to achieve certain advantages, the image guided interventional system is preferably a separate system capable of communicating with any imager. However, it may be, in whole or in part, incorporated into an imager or distributed on a network to be shared with other imagers. Computer 24 receives diagnostic images from scanner 12. The images can be transmitted according to standard formats and protocols. The computer receives location information from a tracking system 28. The tracking system, which is also sometimes referred to as a localizer, includes sensors for detecting the position of objects. The tracking system preferably relies on markers placed on the objects that are readily detectable by the sensors. The sensors and markers could be, for example, optical, acoustical, magnetic or some other type. The markers are arranged in a known geometric relationship with respect to each other and the object. Typically three or more markers are used. The computer system processes and displays the diagnostic images on visual display 20. It also displays and continually updates the position of a representation of an interventional instrument 30 relative to the images. An example of an interventional instrument includes a biopsy needle. The position and orientation of the interventional instrument 30 is determined by tracking system 28 using an instrument tracker 31 comprised of a plurality of markers arranged in a known geometry and having a known relationship to the instrument's axis and end point.

The positions of a patient on platform 16 and of the imager's scanner 12 are preferably also tracked by the tracking system 28 and provided to the computer. Reasons for this are explained in connection with FIGS. 3, 4 and 5. To track the position of the patient, a patient tracker 32 is mounted in such a way that it moves with the patient as table 16 is moved into and out of the gantry of the imager. The patient tracker includes an array of markers that can be sensed (detected) by the tracking system. For some procedures it may be enough to mount the patient tracker to the scanner table, as shown. Otherwise, the patient marker can be affixed as a reference to the patient either invasively or non-invasively. Patient tracker 32 is also mounted in a manner that permits it to be sensed by tracking system 28 while inside the gantry. The position of the scanner 12 is tracked using a scanner tracker 34. The scanner tracker is affixed to the gantry or housing of scanner 12, or incorporated into an imager at any location that remains fixed relative to the scans. The scanner tracker also includes an array of markers that can be detected by tracking system 28. The scanner tracker may be in the form of a plate, to which the markers are affixed, or some other structure.

In a preferred embodiment, which is illustrated, the tracking system is an optical system that uses, as sensors, optical cameras 36 to locate and track movement of optical markers 37. In order to improve detection of the markers, the tracking system preferably operates in the infrared spectrum, with optical markers 37 emitting infrared radiation at intensities substantially greater than the background or other objects in the area so that they can be easily identified by the tracking system. Markers may either be active or passive. In order to emit infrared energy passive markers are provided with a surface that tends to be much more reflective of infrared energy and are formed (in the shape of a sphere, for example) to reflect infrared energy in all directions. Infrared energy is supplied from one or more sources that bathe or suffuse the area with infrared energy. Alternatively, active markers can be used. Active markers generate infrared radiation from electricity.

Passive, infrared markers are presently preferred. Although optical systems are presently preferred, other types of tracking systems could be used instead, including without limitation magnetic, acoustic, fiber optic, and other systems that may now exist or be later developed.

Figure 3:
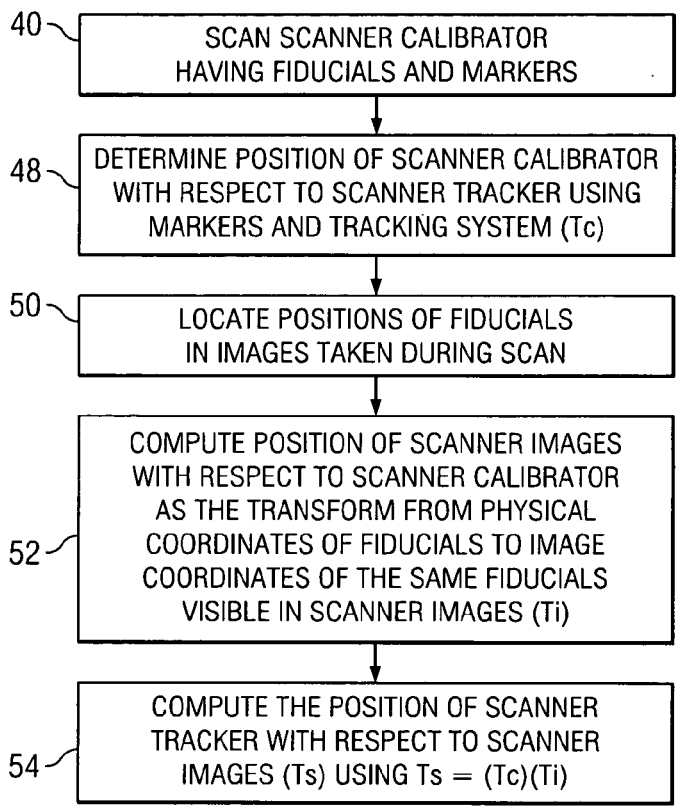
FIG. 3 is a flow diagram of a calibration process for an imager for use with an image guided interventional system.

Referring now also to FIG. 3, imager 10 is "calibrated" according to calibration process 38, meaning that a transform is determined for mapping or relating points or coordinates in images taken by the imager (referred to herein as scanner images) to the position of the imager as represented by scanner tracker 34. A transform is a mathematical function that maps a set of homogeneous coordinates in one coordinate space to another set of homogeneous coordinates in another coordinate space. Once calibrated, the image guided interventional system is capable of registering images from imager 10 to the patient by knowing the positions of scanner tracker 34 and patient tracker 32. Calibration enables an image guided interventional system 22 to be used with other imagers. Once an imager is calibrated, it does not need to be recalibrated unless scanner tracker 34 is moved, though periodic recalibration may be desirable to ensure that the calibration remains accurate.

Figure 4:
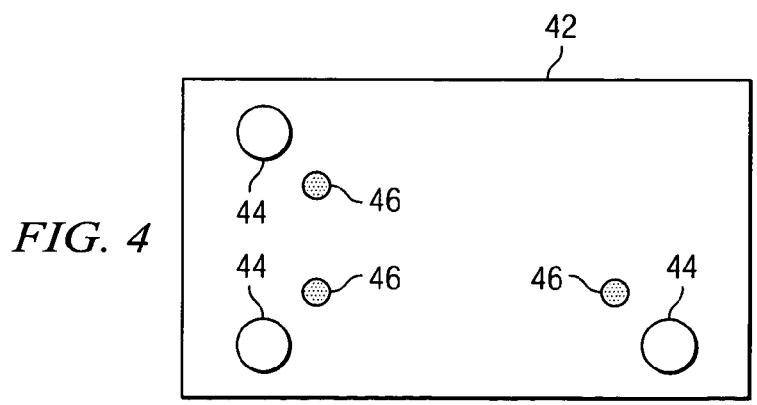
FIG. 4 is an illustration of a calibrator for the process of FIG. 3.

As indicated at step 40, calibration involves taking images of a scanner calibrator. An example of a scanner calibrator is shown in FIG. 4. It includes a base or structure 42, on which are mounted a plurality of markers 44, the positions of which can be detected by tracking system 28. The plurality of markers has a known geometry and relationship with respect to an array of fiducials 46 set in or mounted to base 42. The fiducials are of a type that can be seen or are visible in images taken by imager 10 and whose positions can be accurately localized in those images.

Figure 5:
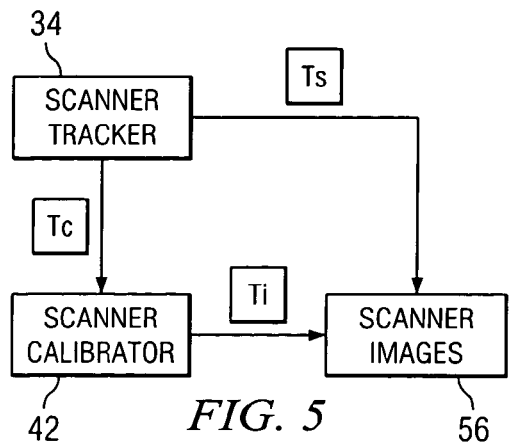
FIG. 5 is a schematic representation of spatial relationships between a scanner tracker, a scanner calibrator and images generated by a scanner.

At step 48, a transform relating the position of the scanner calibrator 42 to the scanner tracker 34 is determined by the image guided surgery system 22 using location information provided by tracker system 28 using the markers present on the calibrator and tracker. This transform will be designated as $T_c$. At step 50, the fiducials in the images are located. Knowing the relationship between the fiducials and the markers on the scanner calibrator 42 allows the physical positions of the fiducials to be determined. Thus, at step 52, a transform designated $T_i$ can be computed that relates or maps the physical location of the fiducials 46 to the positions of the fiducials in the images of the scanner calibrator. A transform $T_s$ for relating the position of scanned images to the position of the scanner tracker 34 can be determined at step 54 using the previously determined transforms $T_i$ and $T_c$, according to the equation $T_s = T_c T_i$. FIG. 5 illustrates the relationship between the positions of the scanner calibrator 42, the scanner images 54 and scanner tracker 34.

Figure 6:
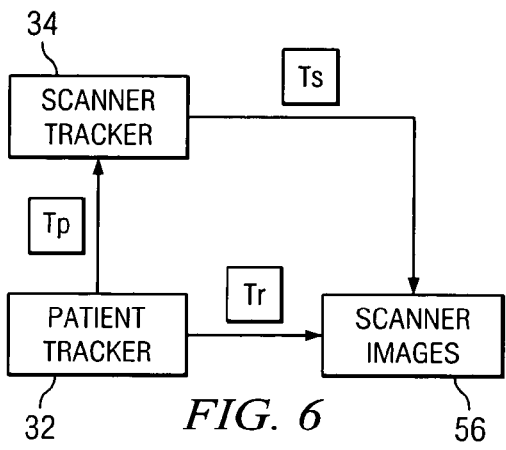
FIG. 6 is a schematic representation of spatial relationships between a scanner tracker, a patient tracker and images generated by a scanner.

With the transform $T_s$, a transform for mapping images from a scanner taken during an interventional procedure to patient tracker 32 can be determined based on the locations of the patient tracker 32 and the scanner tracker 34, as indicated in FIG. 6. This process is referred to as registration, as it registers the images to the patient. With a registration transform, points in the images can be mapped to physical points in the patient's frame of reference. The transform between scanner tracker 34 and patient tracker 32 is designed $T_p$. The transform $T_s$, between scanner tracker 34 and the scanned images was determined during calibration and stored in the memory of the image guided interventional system. Thus, the transform $T_r$ between patient tracker 32 and images from the scanner can be found according to the following relationship: $T_r = T_p T_s$. There is no need for an explicit patient registration step. Registration of the patient to the images using this indirect or implicit process allows the actual position of instrument 30 with respect to the patient to be accurately displayed on the images.

Figure 7:
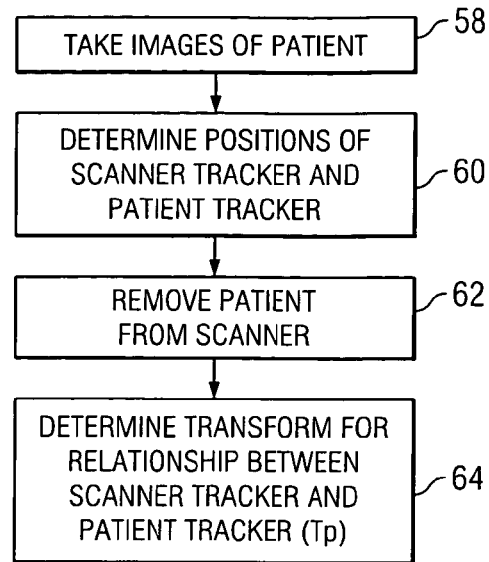
FIG. 7 is a flow diagram of an automatic process for registering images from a scanner to a patient.

Referring now also to FIG. 7, an operator therefore need only acquire an initial scan of a patient at step 58 and move the patient out of the scanner at step 62 before conducting an interventional procedure. Before the patient is removed from the scanner, the image guided interventional system determines at step 60 the locations of the patient tracker 32 and scanner tracker 34. The system then computes at step 64 a transform for relating patient tracker 32 to the scanner tracker 34. Using this transform and the transform $T_s$ determined during calibration, a transform Tr relating patient tracker 32 to the acquired images is computed at step 66 in the manner described above.

Figure 8:
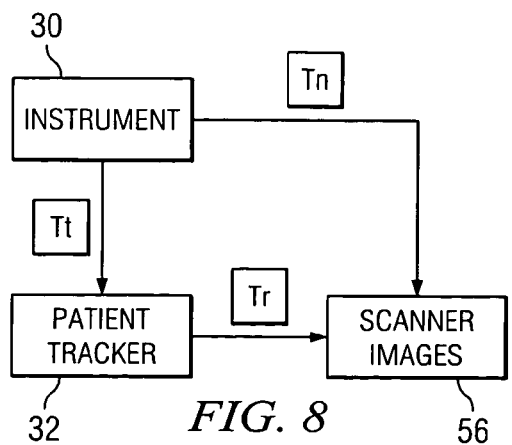
FIG. 8 is a schematic representations of spatial relationships between an instrument, a patient tracker and images from a scanner.

After the registration, as generally indicated by step 68, the person performing the procedure may begin navigating the instrument using a representation of the position of the instrument (e.g. its axis or trajectory and end point) overlaid by the computer 26 on one or more of the acquired images and continuously updated. The images are shown on display 20 next to the patient and in view of the person performing the procedure. In order to overlay onto the images from the scanner a representation of the position of the instrument, a transform $T_n$ between the instrument and scanner images is computed using the relationships illustrated in FIG. 8. The relationship Tt between patient tracker 32 and instrument 30 is known from tracker system 28. The instrument's position is related to the position of instrument tracker 31 (FIG. 1) by a calibration transform that is not shown. The transform $T_r$, between patient tracker 32 and scanner images 56 was calculated at step 66 in FIG. 7. The transform $T_n$ is equal to the product of $T_t T_r$.

Some of the interventional procedures with which the invention may be used include, without limitation, biopsy, vertebroplasty, brachytherapy, facet injections, pain therapy treatments and other.

The invention claimed is:

1. A method for displaying information during an interventional procedure, comprising:

scanning a scanner calibrator to acquire an image of said scanner calibrator, said scanner calibrator comprising at least one fiducial and said image of said scanner calibrator comprising a representation of said at least one fiducial;

determining a position relative to a tracking system of the scanner calibrator when the image of the scanner calibrator was acquired;

determining a position relative to the tracking system of a scanner tracker fixed to a scanner;

determining a transform ($T_c$) between said scanner calibrator and said scanner tracker from the determined positions of the scanner calibrator and the scanner tracker;

calculating a transform ($T_i$) that maps a location relative to the tracking system of said at least one fiducial to a position of said representation of said at least one fiducial in the image of the scanner calibrator;

calculating a transform ($T_s$) between said scanner tracker and said image of said scanner calibrator based at least in part on said determined transform ($T_c$) between said scanner calibrator and said scanner tracker and said calculated transform ($T_i$) mapping said location of said at least one fiducial to said position of said representation of said at least one fiducial in the image of the scanner calibrator;

scanning at least a portion of an anatomy of a patient to acquire a plurality of anatomical images of said portion of said anatomy;

determining a position relative to the tracking system of a patient tracker associated with the patient;

calculating a transform ($T_p$) between said patient tracker and said scanner tracker;

determining a transform ($T_r$) between said patient tracker and said plurality of anatomical images based at least in part on said transform ($T_p$) between said patient tracker and said scanner tracker and at least in part on said transform ($T_s$) between said scanner tracker and said image of said scanner calibrator;

determining a transform ($T_t$) between an instrument used in said interventional procedure and said patient tracker;

calculating a transform ($T_n$) between said instrument and said plurality of anatomical images based at least in part on said determined transform ($T_t$) between said instrument and said patient tracker and said determined transform ($T_r$) between said patient tracker and said plurality of anatomical images; and displaying an updated current position of said instrument on at least one of said plurality of anatomical images based at least in part on said calculated transform ($T_n$) between said instrument and said plurality of anatomical images.

2. A system for displaying information during an interventional procedure, comprising:
- a scanner operable to scan at least a portion of an anatomy of a patient to acquire a plurality of scanner images of said portion of said anatomy;
- a tracking system operable to detect a position of said patient;
- an image guided interventional system having associated application logic operable to:
  - control the scanner to scan a scanner calibrator to acquire at least one image of said scanner calibrator, said scanner calibrator comprising at least one fiducial and said at least one image of said scanner calibrator comprising a representation of said at least one fiducial;
  - determine a first transform between said scanner calibrator and a scanner tracker associated with the scanner;
  - calculate a second transform that maps a location of said at least one fiducial to a position of said representation of said at least one fiducial; and
  - calculate a third transform between said scanner tracker and said at least one image of said scanner calibrator based at least in part on said first transform and said second transform.

3. The system of claim 2 where the application logic is further operable to:
- receive said plurality of scanner images of said portion of said anatomy;
- determine a position of a patient tracker associated with said patient;
- calculate a fourth transform between said patient tracker and said scanner tracker;
- determine a fifth transform between said patient tracker and said plurality of scanner images of said portion of said anatomy based at least in part on said fourth transform and said third transform;
- determine a relationship between an instrument used in said interventional procedure and said patient tracker; and
- calculate a sixth transform between said instrument and said plurality of scanner images of said portion of said anatomy based at least in part on said determined relationship between said instrument and said patient tracker and said determined fifth transform; and further including:
- a display device operable to display an updated current position of said instrument on at least one of said plurality of scanner images of said portion of said anatomy based at least in part on said calculated sixth transform.

4. The system of claim 3, further comprising an instrument tracker affixed to said instrument.

5. The system of claim 3, wherein said patient tracker is mounted on a table of said medical imaging system.

6. The system of claim 3, wherein said patient tracker is invasively affixed to said patient.

7. The system of claim 3, wherein said patient tracker is non-invasively affixed to said patient.

8. The system of claim 3, wherein the scanner tracker is affixed to said scanner.

9. A computer-readable medium having stored thereon an instruction set to be executed, the instruction set, when executed by a processor, causes the processor to:
- determine a transform between a calibration image of a scanner calibrator having at least one imageable fiducial and a scanner in which the calibration image is generated;
- receive a plurality of anatomical images of a portion of an anatomy of a patient for use during an interventional procedure generated by the scanner;
- determine a position of a patient tracker associated with said patient;
- calculate a transform between said patient tracker and the scanner which generates the anatomical images;
- determine a transform between said patient tracker and said plurality of anatomical images based at least in part on said transform between said patient tracker and said scanner and at least in part on the transform between the calibration image and said scanner;
- determine a current relationship between an instrument used in said interventional procedure and said patient tracker;
- calculate a current transform between said instrument and said plurality of anatomical images based at least in part on said determined current relationship between said instrument and said patient tracker and on said determined transform between said patient tracker and said plurality of anatomical images; and
- cause display of an updated current position of said instrument on at least one of said plurality of anatomical images based at least in part on said calculated current transform between said instrument and said plurality of anatomical images.

10. The computer-readable medium of claim 9, wherein the instruction set, when executed by the processor, further causes the processor to calculate a transform between said patient tracker and a scanner tracker associated with said scanner.

11. The computer-readable medium of claim 9, wherein the instruction set, when executed by the processor, further causes the processor to calculate a transform between said scanner and at least one image of a scanner calibrator associated with said scanner.

12. The computer-readable medium of claim 9, wherein the instruction set, when executed by the processor, further causes the processor to calculate a transform between a scanner tracker associated with said scanner and the scanner calibrator.

13. The computer-readable medium of claim 12, wherein the instruction set, when executed by the processor, further causes the processor to determine said transform between said patient tracker and said plurality of anatomical images based at least in part on said calculated transform between said scanner tracker and said calibration image.

14. The computer-readable medium of claim 12, wherein the instruction set, when executed by the processor, further causes the processor to:
- scan said scanner calibrator to acquire said calibration image;
- determine a transform between said scanner calibrator and said scanner tracker;
- calculate a transform that maps a location of said at least one imageable fiducial to a position of a representation of said at least one imageable fiducial in the calibration image; and
- calculate said transform between said scanner tracker and said calibration image based at least in part on said determined transform between said scanner calibrator and said scanner tracker and said calculated transform mapping said location of said at least one imageable fiducial to said position of said representation of said at least one imageable fiducial in the calibration image.

15. A method for indicating, relative to a scanner image of a portion of a patient's anatomy, a position of an instrument being used in the vicinity of the patient while a patient remains on a scanning table of a scanner that took the scanner image, the method comprising: receiving at least one scanner image of a portion of the anatomy of a patient taken by a scanner; receiving an indication of a position of a patient tracker, the position of the patient tracker being indicative of a position of the patient; determining a spatial relationship between the patient tracker and the scanner based at least in part on a known position of the scanner; determining a spatial relationship between the patient tracker and the at least one scanner image based at least in part on the spatial relationship between the patient tracker and the scanner and at least in part on a known spatial relationship of the scanner relative to the at least one scanner image; receiving an indication of a position of an instrument; determining a spatial relationship between the instrument and the patient tracker; determining a spatial relationship between the instrument and the at least one scanner image based at least in part on the spatial relationship between the instrument and the patient tacker and the spatial relationship between the patient tracker and the at least one scanner image; and visually displaying the spatial relationship between the position of the instrument and the at least one scanner image.

16. The method of claim 1 wherein determining a position of the patient tracker includes:
    determining a position of the patient tracker when the portion of the anatomy is scanned; and
    determining a position of the patient tracker after the patient is moved from the anatomy scanning position into a position in which the interventional procedure is performed.

* * * * *